United States Patent [19]

Merrill, deceased et al.

[11] Plant 4,398

[45] Mar. 20, 1979

[54] PEACH TREE

[76] Inventors: Grant Merrill, deceased, late of Red Bluff, Calif.; by Lucile B. Merrill, executrix, 325 Breese Ave., Red Bluff, Calif. 96080

[21] Appl. No.: 888,692

[22] Filed: Mar. 20, 1978

[51] Int. Cl.[2] ..... A01H 5/03
[52] U.S. Cl. ..... Plt./43
[58] Field of Search ..... Plt./43

*Primary Examiner*—Robert E. Bagwill
*Attorney, Agent, or Firm*—Roger B. Webster

[57] ABSTRACT

A peach tree which is of medium size, medium vigor, upright to spreading, open, vase-formed, hardy, foliated with medium size, lanceolate to almost ovate-lanceolate, acutely pointed, long, tapering leaves having a finely serrate margin, short petiole, and opposite, reniform glands, blooms early to medium with medium size, broad ovate, showy, pink flowers, and a regular and very productive bearer of large, uniform, slightly unsymmetrical, broadly truncate-globose, late ripening, freestone fruit having yellowish green to yellowish skin blushed with dull grayish red, and yellow flesh, the surface of the pit cavity being red.

6 Drawing Figures

BACKGROUND OF THE VARIETY

1. Field of the Invention

In an extensive plant breeding program, Grant Merrill, originator and now deceased, originated a large number of new and distinct varieties of fruit trees, and which included the herein-claimed variety of peach tree. Such plant breeding program was undertaken in originator's experimental orchard located near Exeter, Tulare County, Calif.

2. Prior Varieties

Among the existent varieties of peach trees which were known to originator, particular reference is made to the Autumn Gem (U.S. Plant Pat. No. 3,582).

ORIGIN OF THE VARIETY

The present variety of peach tree was originated, in the aforesaid experimental orchard, as an open-pollinated seedling of the Autumn Gem.

ASEXUAL REPRODUCTION OF THE VARIETY

When such open-pollinated seedling matured as a bearing tree, and it was determined to be of commercial value, the variety was asexually reproduced, on originator's behalf, by a commercial nursery, located at Madera, Madera County, Calif.; such reproduction having been accomplished by grafting on suitable rootstock. The asexual reproduction of the variety ran true, in all respects, to the original tree of the variety.

SUMMARY OF THE VARIETY

The herein-claimed new and distinct varity of peach tree is of medium size, medium vigor, upright to spreading, open, vase-formed, hardy, foliated with medium size, lanceolate to almost ovate-lanceolate, acutely pointed, long, tapering leaves having a finely serrate margin, short petiole, and opposite, reniform glands, blooms early to medium with medium size, broad ovate, showy, pink flowers, and a regular and very productive bearer of large, uniform, slightly unsymmetrical, broadly truncate-globose, late ripening, freestone fruit having yellowish green to yellowish skin blushed with dull grayish red, and yellow flesh, the surface of the pit cavity being red.

The herein-claimed new and distinct variety of peach tree is characterized—in particular comparison with the Autumn Gem—by fruit which, while similar in size and skin color, is in harvest approximately two weeks later.

BRIEF DESCRIPTION OF THE DRAWING

The drawing is an illustration, by photographic reproduction in color, depicting fruit of the variety; certain of such fruit being shown whole, while others are cut into halves with the stone remaining in place in one of the related halves.

DESCRIPTION OF THE VARIETY

The botanical details of this new and distinct variety of peach tree—with color definitions (except those in common color terms) referenced to Maerz and Paul Dictionary of Color—are as follows:

Tree:
- *Size.*—Medium.
- *Vigor.*—Medium.
- *Growth.*—Upright to spreading.
- *Density.*—Open.
- *Form.*—Vase-formed.
- *Hardiness.*—Hardy.
- *Production.*—Very productive.
- *Bearing.*—Regular bearer.

Trunk:
- *Size.*—Medium. '*Texture.*—Medium.

Branches:
- *Size.*—Medium.
- *Texture.*—Medium.
- *Color.*—Young Branches — dull gray-brown (16-H-10). Mature branches — dull gray-brown (16-H-8).
- *Lenticels.*—Number — Medium. Size — Medium.

Leaves:
- *Size.*—Medium. Average length — 6". Average width — 2 7/16".
- *Form.*—Lanceolate to almost ovate-lanceolate. Long, tapering, acutely pointed.
- *Thickness.*—Medium.
- *Color.*—dark green. Ventral surface — dark green (31-E-12). Dorsal surface.— lighter green (21-F-6).
- *Texture.*—Smooth.
- *Margin.*—Finely serrate.

*Petiole.*—Short — average ⅜". Medium thick.
*Glands.*—Number — 2 to 4. Opposite. Medium size. Reniform. Positioned on petiole and base of blade.
*Stipules.*—Early deciduous.

Flower buds:
*Hardiness.*—Hardy.
*Size.*—Medium.
*Length.*—Medium.
*Form.*—Obtuse — conic.
*Pubescence.*—Pubescent.

Flowers:
*Blooming period.*—Date of first bloom Mar. 4, 1977. Date of full bloom Mar. 11, 1977. Early — medium, as compared with other varieties.
*Size.*—Medium — 18–20 mm. long × 15–17 mm. broad.
*Shape.*—Broad ovate.
*Appearance.*—Showy.
*Color.*—Pink (1-C-1) apically shading to deeper pink (1-F-5) basally.

Fruit:
*Maturity when described.*—Hard - Oct. 21, 1977.
*Date of first picking.*—Oct. 17, 1977.
*Date of last picking.*—Oct. 25, 1977.
*Size.*—Uniform. Large. Average diameter axially — 3⅛". Average transversely in suture plane 3 3/16".
*Form.*—Uniform. Slightly unsymmetrical. Broadly truncate-globose. Slightly compressed toward suture.
*Suture.*—An inconspicuous line with marked depression beyond pistil point.
*Ventral surface.*—Rounded slightly. Lipped throughout.
*Lips.*—Equal to unequal.
*Cavity.*—Flaring. Circular. Depth — ⅝" to ¾". Breath—1⅜". *Markings.*—Wanting.
*Base.*—Truncate.
*Apex.*—Rounded to truncate.
*Pistil point.*—slightly oblique.

Skin:
*Thickness.*—Medium.
*Texture.*—Medium.
*Tenacity.*—Tenacious to flesh.
*Tendency To Crack.*—None.
*Color.*—Ground color — yellowish green (20-K-1) to yellowish (10-K-3). Blush — Semi-washed to washed, but predominantly spotted, with short stripes. Grayish red (6-H-2) to (6-H-3). Spots and stripes — red (7-J-7).

*Down.*—Moderate. Short. Does not roll up when rubbed.

Flesh:
*Color.*—Yellow (10-J-2). Surface of pit cavity — red (4-L-6).
*Amygdalin.*—Moderate.
*Juice.*—Moderate.
*Texture.*—Crisp. Meaty.
*Fibers.*—Few. Fine. Tender.
*Ripens.*—Evenly.
*Flavor.*—Sub-acid. Mild.
*Aroma.*—Slight.
*Eating quality.*—Good.

Stone:
*Type.*—Free.
*Size.*—Large to medium. Average length — 1 9/16" Average breadth — 1 1/16" Average thickness — ¾".
*Form.*—Elliptical.
*Base.*—Oblique.
*Hilum.*—Narrow. Oval.
*Apex.*—Acuminate.
*Sides.*—Unequal. Curved more on dorsal suture.
*Surface.*—Irregularly furrowed near base. Pitted throughout.
*Ridges.*—Rounded.
*Pits.*—Circular to elongated.
*Ventral edge.*—Medium thickness. Without wing throughout.
*Dorsal edge.*—Narrow, with deep, narrow groove to above center.
*Color.*—Dark brown, stained red at base and along sutures, especially ventral.
*Tendency to split.*—None.

Use: Market. Dessert.
Keeping quality: Good.
Resistance to insects and diseases: Good.
Shipping quality: Good.

The peach tree and its fruit herein described may vary in slight detail due to climatic and soil conditions under which the variety may be grown; the present description being of the variety as grown in the Central Valley of California.

I claim:

1. A new and distinct variety of peach tree, substantially as illustrated and described, particularly characterized by freestone fruit which—in particular comparison with the Autumn Gem—is similar in size and skin color but is in harvest approximately two weeks later.

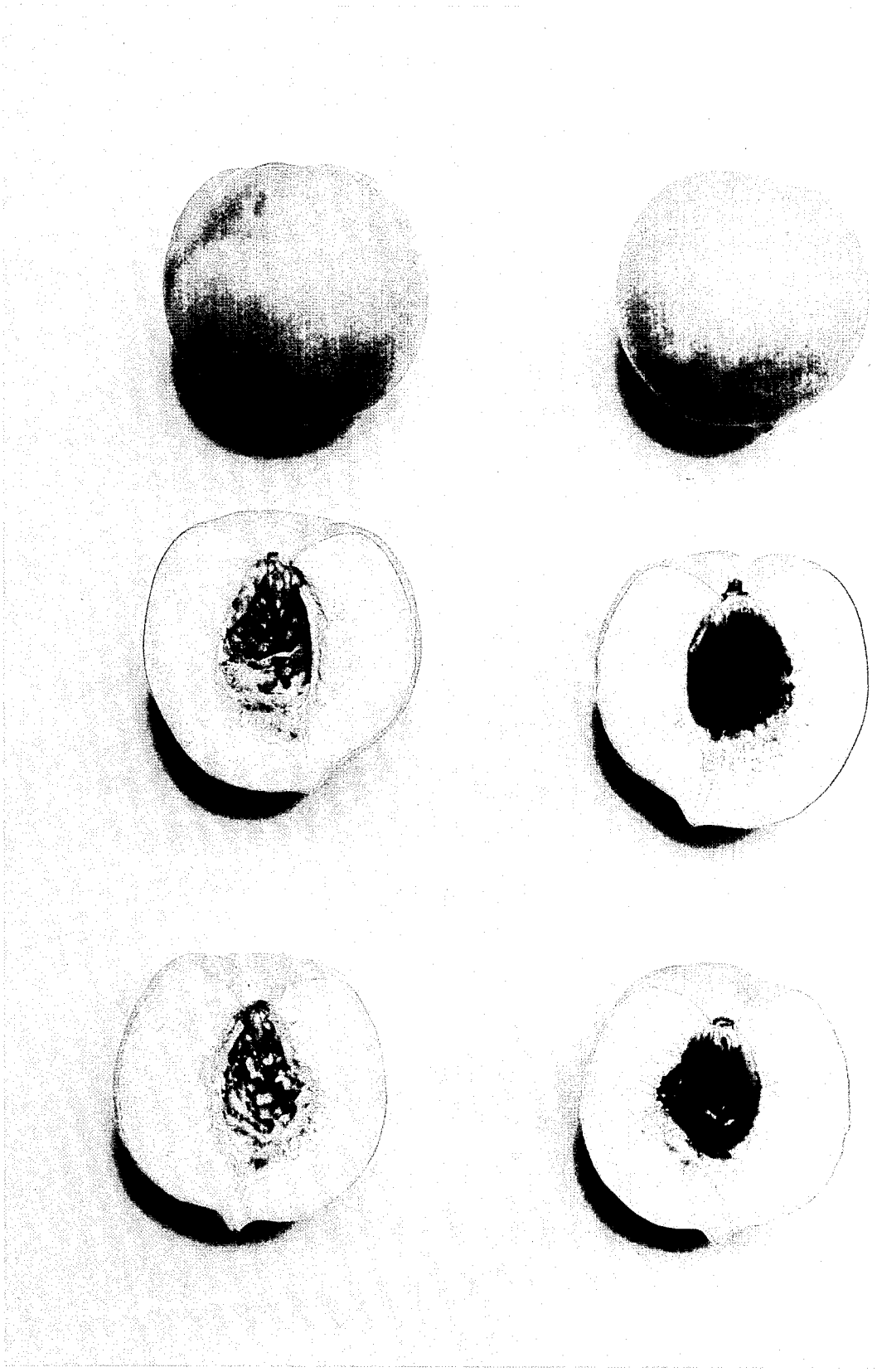

* * * * *